United States Patent [19]

Huang

[11] 4,276,055
[45] Jun. 30, 1981

[54] NOVEL FUEL COMPOSITION AND THE PROCESS OF PREPARING SAME

[76] Inventor: James P. H. Huang, 3-4, Alley 16, La. 64, Sec. 2, Chung Shen Rd., Chung Ho City, Taiwan

[21] Appl. No.: 78,059

[22] Filed: Sep. 24, 1979

Related U.S. Application Data

[63] Continuation-in-part of Ser. No. 72,682, Sep. 5, 1979, abandoned.

[51] Int. Cl.³ .............................................. C10L 1/02
[52] U.S. Cl. .................................................... 44/53
[58] Field of Search ........................ 44/53; 568/594; 260/603 C

[56] References Cited

U.S. PATENT DOCUMENTS

| | | | |
|---|---|---|---|
| 1,609,593 | 12/1926 | Woodruff et al. | 260/449.5 |
| 1,797,569 | 3/1931 | Edmonds et al. | 260/449.5 |
| 1,875,714 | 9/1932 | Edmonds | 260/449.5 |
| 2,451,949 | 10/1948 | Heinemann | 568/594 |
| 2,663,742 | 12/1953 | Frevel et al. | 568/594 |
| 2,682,560 | 6/1954 | Carter et al. | 260/603 C |
| 2,691,685 | 10/1954 | Frevel et al. | 568/594 |
| 3,711,253 | 1/1973 | Rothert et al. | 260/603 C |
| 3,932,522 | 1/1976 | Seither et al. | 260/603 C |
| 3,955,939 | 5/1976 | Sommer et al. | 44/53 |

Primary Examiner—Winston A. Douglas
Assistant Examiner—Y. Harris-Smith
Attorney, Agent, or Firm—Tak Ki Sung

[57] ABSTRACT

This invention provides a novel synthetic fuel composition suitable for use in internal combustion engines. The fuel composition comprises from about 40 to 95% by volume of a primary alcohol having 1–4 carbon atoms, from about 5 to 60% by volume of an alcohol derivative having the general formula

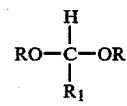

wherein R is $-CH_3$, $-C_2H_5$, $-C_3H_7$, or $-C_4H_9$, and $R_1$ is hydrogen or $-CH_3$.

The fuel composition can be prepared by reacting a primary alcohol having 1–4 carbon atoms with oxygen or air to form an alcohol derivative which is an aldehyde and reacting the aldehyde with an additional portion of the alcohol to form the product, comprising the alcohol, the alcohol derivative and the aldehyde.

16 Claims, 1 Drawing Figure

FLOW SHEET

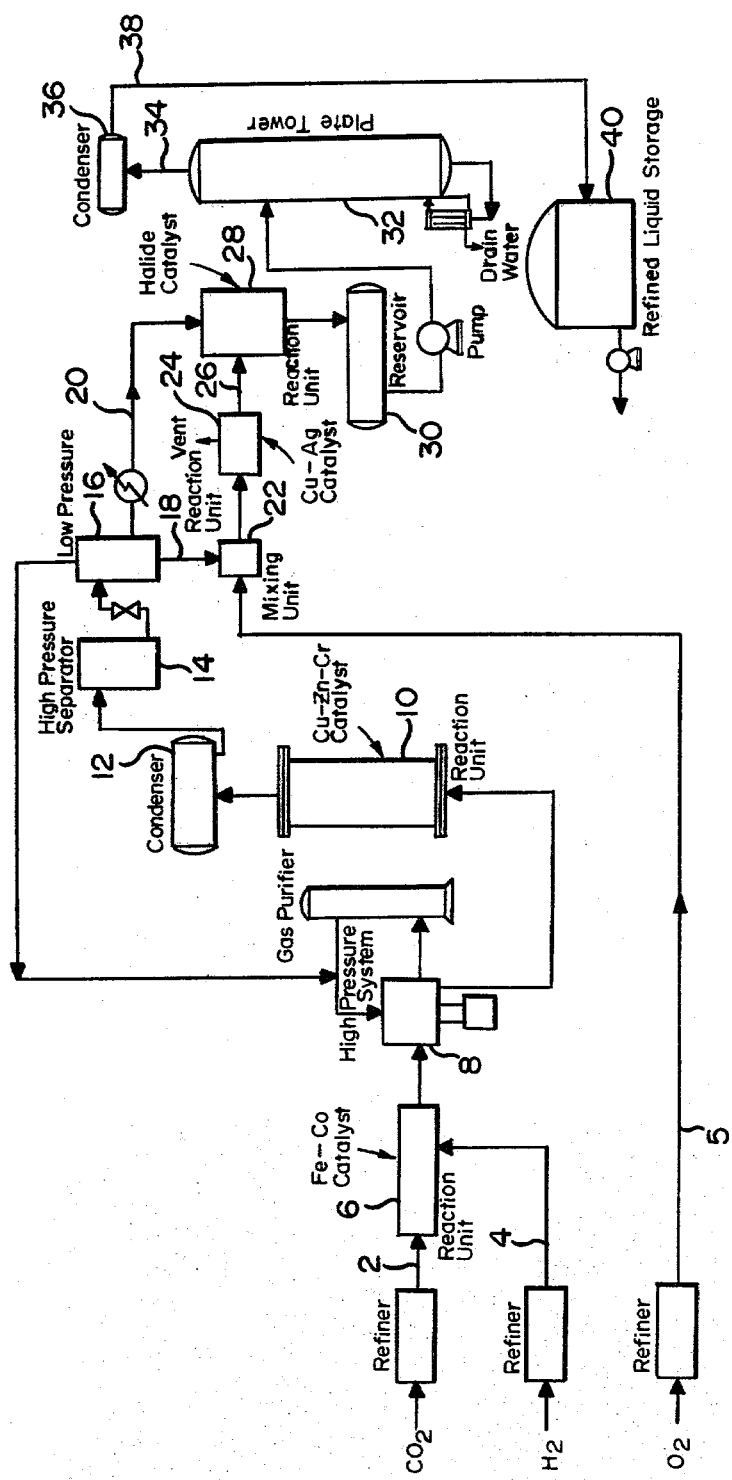

NOVEL FUEL COMPOSITION AND THE PROCESS OF PREPARING SAME

This application is a continuation-in-part application of U.S. Application Ser. No. 72,682, filed Sept. 5, 1979, now abandoned.

FIELD OF THE INVENTION

The present invention relates to a novel fuel composition. More particularly, the present invention relates to a fuel composition which is suitable for use in internal combustion engines and which can be prepared from readily available raw materials such as carbon dioxide and water. In addition, this invention relates to a process of preparing the novel fuel composition.

BACKGROUND OF THE INVENTION

Fuels to substitute the conventional gasoline and processes for producing such fuels have been much investigated. For many years, gasoline has been considered as the most ideal fuel for the internal combustion engine. Although gasoline has contributed much to modern life, the scarcity of supply has also caused the so called energy crisis during recent years. Besides, waste gases from automobiles pollute the environment and have become a public nuisance. Research for fuel substitutes has been launched with vast investment in many countries around the world. Some processes have been disclosed in scientific journals patents and other publications. However, low production yield, difficulties in obtaining raw materials, high complexity and cost of the equipment or the necessity of altering the fuel system in the engine or carburetor using the product have made such substitutes impractical. New fuels claimed to be directly usable as gasoline or to be mixed with gasoline still inherit the drawbacks of polluting the environment and usually require the alteration of the engine, the fuel intake system and the addition of specially designed carburetors. It is known that alcohols including methanol, ethanol propanol or mixtures thereof can be used as substitutes for gasoline. Results obtained were not satisfactory. Efforts have been made in many countries to solve the problems involved. Therefore, there exists a need to formulate a synthetic fuel as a substitute for gasoline, the synthetic fuel being economic to produce as well as being free from harmful byproducts which would pollute the environment.

SUMMARY OF INVENTION

The present invention provides a synthetic fuel composition and the process for producting same. The fuel composition can be prepared from raw materials such as carbon dioxide and water, which are readily available, to form an alcohol which is then oxidized to form an aldehyde. The aldehyde is further reacted with the alcohol to form the fuel composition.

BRIEF DESCRIPTION OF DRAWING

The drawing shows a flow sheet depicting the process of the present invention.

DETAILED DESCRIPTION OF THE INVENTION

According to the present invention a fuel composition comprising (a) from about 40% to 95% by volume of a primary alcohol having 1 to 4 carbon atoms, and (b) from about 5% to 60% by volume of a compound having the general formula

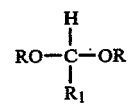

Wherein R is $-CH_3$, $-C_2H_5$, $-C_3H_7$, or $-C_4H_9$, and $R_1$ is hydrogen or $-CH_3$, and (c) from about 0.001% to 1% by volume of an aldehyde having the general formula

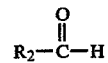

wherein $R_2$ is hydrogen, $-CH_3$ or $-C_2H_5$. The fuel composition can be used as a substitute for gasoline in interal combustion engines.

The present fuel composition comprises from about 40% to 95% by volume of a primary alcohol having 1 to 4 carbon atoms. Preferably, the composition comprises from about 40% to 85% and most preferably 40% to 50% by volume of the primary alcohol. Useful examples of the alcohol include methanol, ethanol, propanol and butanol. Among these alcohols, methanol and ethanol are preferred. Particularly, methanol is the most preferred alcohol since its supply is plentiful and it can be obtained at low cost.

In addition, the present composition comprises from about 5 to 60%, preferably from about 15% to 60%, and most preferably from about 50% to 60% by volume of a compound having the formula

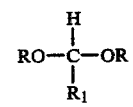

wherein R is methyl, ethyl, propyl or butyl and $R_1$ is hydrogen or methyl. Preferably, R is methyl or ethyl, and $R_1$ is hydrogen or methyl.

In other words, the preferred compounds are:

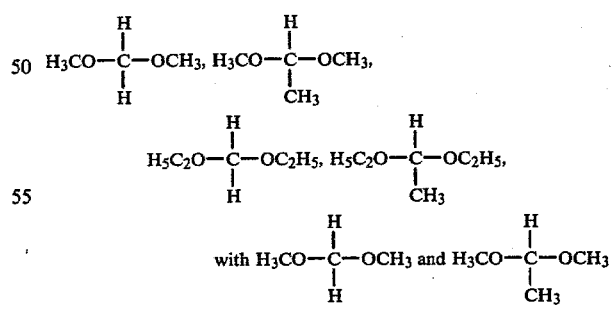

being most preferred.

Further, the present composition comprises from about 0.001 to 1% of an aldehyde having the formula

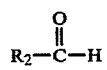

wherein $R_2$ is hydrogen or methyl. Examples of the aldehyde are formaldehyde and acetaldehyde, with formaldehyde being preferred.

In accordance with the above a, preferred embodiment of the present invention is as follows:

| Embodiment | |
|---|---|
| Component | % by volume |
| (a) methanol | 49.5 |
| (b) $H_3CO-\underset{\underset{H}{\vert}}{\overset{\overset{H}{\vert}}{C}}-OCH_3$ | 50.0 |
| (c) $H-\overset{\overset{O}{\parallel}}{C}-H$ | 0.5 |

The present invention also relates to a process of preparing the synthetic fuel composition described above. The process comprises:

(1) reacting an aldehyde having the general formula $$H-\overset{\overset{O}{\parallel}}{C}-R$$

wherein R is hydrogen or methyl, the aldehyde being in the form of a vapor or liquid, with (2) a primary alcohol having 1 to 4 carbon atoms in the presence of a gaseous halide catalyst, the alcohol being in the form of a vapor or a liquid.

The reaction is conducted at a temperature of from about 70° C. to 300° C., preferably from about 70° C. to 200° C., and most preferably from about 70° C. to 90° C., and a pressure of from about 2 to 10 atm., preferably from about 2 to 5 atm., most preferably from about 2 to about 3 atm. The molar ratio of aldehyde to alcohol is from about 2-4:1, preferably from about 2-3:1, and most preferably from about 2.2:1. It is noted that the alcohol should be in excess of the stoichiometric amount. The catalyst is present in an amount of less than 1% by volume of the total reaction mixture. The catalyst is a gaseous halide. Examples of useful catalysts include hydrogen fluoride and hydrogen chloride, with hydrogen chloride being preferred. The reaction time is from about 0.5 to 2 seconds, preferably from about 0.5 to 1 second.

In the above reaction, it is important to note that the aldehyde is preferred to be in the form of a vapor. As to the alcohol, it may be either a liquid or a vapor. The formation of the fuel composition from an alcohol and an aldehyde is believed to be represented by the following equation:

$$2R_3-\overset{\overset{H}{\vert}}{\underset{\underset{H}{\vert}}{C}}-OH + R_4-\overset{\overset{O}{\parallel}}{C}-H \longrightarrow R_3C-O-\overset{\overset{H}{\vert}}{\underset{\underset{R_4}{\vert}}{C}}-O-\overset{\overset{H}{\vert}}{\underset{\underset{H}{\vert}}{C}}OCR_3 + H_2O$$

wherein $R_3$ is hydrogen, methyl, ethyl or propyl and $R_4$ is hydrogen or methyl.

The aldehyde used in the above reaction can be formed by reacting a primary alcohol having 1-4 carbon atoms with oxygen or air. Examples of the alcohol include methanol, ethanol, propanol, and butanol, with methanol and ethanol being preferred, and methanol most preferred.

The aldehyde-forming reaction is conducted at a pressure of from about 2 to 10 atm, preferrably from about 2 to 3 atm and a temperature of from 300° C. to 450° C., preferably from about 380° C. to 400° C. in the presence of an all Cu or Cu-Ag catalyst, molar ratio of Cu:Ag being from about 90-100:1. The reaction time is from about 0.01 to 0.1 second.

In forming the aldehyde, a portion of the alcohol can be used. The remaining portion of the alcohol can be used as a reactant in forming the present fuel composition by reacting the alcohol with the newly formed aldehyde which is preferably in a vapor state. In other words, a given stream of primary alcohol can be divided into two portions. The first portion is used to form the aldehyde. The second portion is used to react with the aldehyde to form the present fuel composition. As to the volume ratio of the first: second portions, this can be varied in accordance with the particular composition of the fuel.

The formation of the present fuel composition as described above can be represented by the following equations:

$$R_5\overset{\overset{H}{\vert}}{\underset{\underset{H}{\vert}}{C}}-OH + \tfrac{1}{2}O_2 \longrightarrow R_5-\overset{\overset{O}{\parallel}}{C}-H + H_2O$$

$$2(R_6\overset{\overset{H}{\vert}}{\underset{\underset{H}{\vert}}{C}}-OH) + R_5\overset{\overset{O}{\parallel}}{C}-H \longrightarrow R_6\overset{\overset{H}{\vert}}{\underset{\underset{H}{\vert}}{C}}-O-\overset{\overset{H}{\vert}}{\underset{\underset{R_5}{\vert}}{C}}-O-\overset{\overset{H}{\vert}}{\underset{\underset{H}{\vert}}{C}}R_6 + H_2O$$

wherein $R_5$ is hydrogen or methyl, and $R_6$ is hydrogen, methyl, ethyl or propyl.

From the above equations, it can be seen that the amount of alcohol used to form the aldehyde and the amount of alcohol used to react with the formed aldehyde can be varied greatly in accordance with the composition of the final fuel product.

The alcohol used in forming the aldehyde can be prepared by such waste material as carbon dioxide. In this connection, as an example, methanol can be formed from carbon dioxide as represented by the following equation:

$$CO_2 + 3H_2 \rightarrow CH_3OH + H_2O$$

The carbon dioxide can be a byproduct formed from the Weizamn process wherein starch is fermented with certain bacteria. The carbon dioxide is reacted with hydrogen in the presence of a Fe catalyst. The reaction is conducted at a pressure of from about 2 to 20 atm and a temperature of from about 325° to 450° C. and a $CO_2$:$H_2$ molar ratio of about 1:3. The reaction is permitted to proceed for a period of from about 0.01 to 0.05 seconds. Thereafter, the gases are transferred to a high pressure reactor where the gases are reacted in the presence of a Cu-Zn-Cr oxides catalyst at a temperature of from about 200° C. to 300° C. and a pressure of from about 100 to 180 atm. The molar ratio of Cu:Zn:Cr oxides is 10:80:10. The methanol produced from the carbon dioxide-hydrogen reaction can then be used to form the aldehyde and fuel composition as described above.

The fuel composition prepared in accordance with the present invention can be used as a substitute for gasoline. In view of the fact that it can be prepared from such raw materials as carbon dioxide, air and methanol which are readily available, the cost of such fuel composition is necessarily much lower than that of gosoline. In addition, the present fuel composition has a lower combustion temperature than gasoline which means that less nitrogen oxides ($NO_x$) are formed, thus causing a decrease in the amount of pollutants in automobile exhaust gases. The present fuel composition also can be completely combusted within an automobile engine to form carbon dioxide and water which cause no harm to the environment.

Other desirable properties of the present fuel composition include a freezing point of below minus 70° C. which ensures operation of the engine even at exceptionally cold temperatures. The present fuel composition boils within the temperature range of from about 40° C. to 180° C. Since water is miscible with the present fuel composition, the presence of a small amount of water therein will not cause fuel line freeze up since the water is dissolved in the fuel. Also, it has been found that an engine is easier to start when the present fuel composition is used.

More importantly, the present fuel composition can be fed to an internal combustion engine without any modification of the engine or the carburetor thereof. Thus, the present fuel composition incurs no extra cost on the operation of the internal combustion engine. As will be shown later in the examples, the milage provided by the present composition is comparable or slightly improved over that of gasoline.

The present invention is further illustrated in the following examples. Since the examples are for illustrative purposes, they are not to be interpreted as limiting.

EXAMPLE 1

This example shows the synthesis of the present fuel composition from carbon dioxide, hydrogen, and oxygen.

With reference to the drawing, 10 mols of refined $CO_2$ gas 2 and 30 mols of refined $H_2$ gas 4 are charged into a low pressure reactor 6 under a pressure of 15 atm. and a temperature of 360° C. Reaction takes place in the presence of a Fe catalyst. The mixed gas is further transfered by a high pressure pump 8 into high pressure reactor 10, where the gases react continuously under a pressure of 160 atm. and a temperature of 330° C. in the presence of a Cu-Zn-Cr oxides catalyst. The methanol vapor leaves reactor 10 and is condensed in condenser 12. Thereafter, the condensed methanol is fed to high pressure separator 14 and then low pressure separator 16. A portion of the gaseous methanol 18 is mixed with oxygen 5 in the proportion of 2:1 in mixer 22 and fed to reactor 24 where the pressure is 2 atm. and temperature is 400° C. to produce an aldehyde gas in the presence of a Cu catalyst. The aldehyde gas 26 is introduced with the remaining portion of the gaseous methanol 20 into reactor 28 where a gaseous halide catalyst is present, to react under a pressure of 2 atm. and a temperature of 80° C. The product is collected in container 30. The product is refined by feeding the product to plate tower 32. The vapor leaves the tower via stream 34 and is condensed in condenser 36. The final liquid product is fed to storage tank 40 via stream 38. 300 ml of a liquid fuel having the following composition is obtained:

| | |
|---|---|
| methanol ($CH_3OH$) | 84.5% by volume |
| aldehyde ($CH_2O$) | 0.5% |
| alcohol derivative ($C_3H_8O_2$) | 15% |

EXAMPLE 2

The process described in Example 1 is repeated, except that the ratio of mixing of the portion of methanol and oxygen is 1:1 instead of 2:1. The results are analysed to show the following composition:

| | |
|---|---|
| methanol | 68% |
| aldehyde | 0.6% |
| alcohol derivative | 31.40% |

EXAMPLE 3

Methanol and ethanol obtained from fermentation are used to replace the methanol produced in the high pressure reaction described in Example 1. The results show no substantial difference.

EXAMPLE 4

1 mol of formaldehyde in vapor form is reacted with 2 mol of methanol in the presence of a gaseous HCl catalyst. The reaction is conducted at a temperature of 80° C. and a pressure of 2 atm. 0.95 mol of an alcohol derivative is obtained. The product is a colorless clear liquid. Analysis of the alcohol derivative shows an empirical formula of $C_3H_8O_2$.

EXAMPLE 5

1 mol of formaldehyde in vapor form is reacted with 2 mol of ethanol in the presence of a gaseous HCl catalyst. The reaction is conducted at a temperature of 85° C. and a pressure of 2 atm. 0.94 mol of an alcohol derivative is obtained. The product is a clear, colorless liquid. Analysis of the alcohol derivative shows an empirical formula of $C_5H_{12}O_2$.

EXAMPLE 6

Example 4 is repeated except 1 mol of acetaldehyde is used. 0.94 mol of an alcohol derivative is obtained. The product is a clear, colorless liquid. Analysis of the alcohol derivative shows an empirical formula of $C_4H_{10}O_2$.

EXAMPLE 7

Example 5 is repeated except 1 mol of acetaldehyde is used. 0.95 mol of an alcohol derivative is obtained. The product is a clear, colorless liquid. Analysis of the alcohol derivative shows an empirical formula of $C_6H_{14}O_2$.

EXAMPLE 8

Liquid fuel of the present invention obtained in Example 4 was mixed with conventional gasoline in a volume ratio of 1:1 and used to drive a Yue Loong model 1200 sedan without any modification of the engine or carburetor. Results of road tests are compared with those of the same car using regular and premiun gasoline as shown in Table 1:

TABLE 1

| test No. | | ignition time required | starting momentum | slope climbing | knocking | milage per liter (km/l) | smoke observed in exhaust | engine temperature as indicated by gauge |
|---|---|---|---|---|---|---|---|---|
| 1 | gasoline regular | ordinary about 3 sec. | acceptable | bad, with rattling noise | serious | 10.3 | yes | medium high |
| 2 | gasoline premium | ordinary about 2 sec. | better | usual | with some rattling | 11.6 | yes | medium high |
| 3 | 50% regular gas, 50% liq. fuel* of the invention (by volume) | fast about 1 sec. | fast, greatly improved | good | none | 11.8 | no | low |

*composition: 49.5% alcohol, 50% alcohol derivative and 0.5% aldehyde.

From the above, it is obvious that the engine using the liquid fuel of the present invention operates at a lower temperature, thus reducing engine trouble due to overheating.

EXAMPLE 9

The liquid fuel of the present invention was used to drive a two cycle 50 cc engine (3% of lube was added to the fuel). Results of performance are compared with those given by the same engine using regular gasoline as shown in Table 2.

It can be seen that the performance of the liquid fuel of the present invention having a composition of $CH_3OH$: 49.5% alcohol derivative: 50%, $CH_2O$: 0.5% gives better results than regular gasoline.

EXAMPLE 10

Various fuel mixtures comprising the liquid fuel of the present invention are used repeatedly to drive one Yue Loong model 1500 sedan having the engine adjusted to cope with particular conditions. The road tests results are tabulated in Table 3 to compare with the results of road tests using premium gasoline and pure methanol.

TABLE 2

| fuel used | property & performance | | | | | |
|---|---|---|---|---|---|---|
| | acceleration sec/10m | speed (km/hr) | horse power (HP) at 3000rpm | at 4000rpm | heat content kcal/1 | octane number |
| gasoline | 4.35 | 40 | 1.41 | 1.72 | 12,100 | 60 |
| liq. fuel of the invention methanol 49.5% alcohol derivative 50% formaldehyde less than 0.5% | 4.00 | 42 | 1.43 | 1.75 | 8,600 | 118 |
| 50% of regular gasoline 50% fuel of the invention (by volume) | 4.10 | 41.5 | 1.42 | 1.73 | 10,200 | 90 |

TABLE 3

| test No. | fuel used | Test of | | | | | | |
|---|---|---|---|---|---|---|---|---|
| | | ignition time required | starting momentum | slope climbing | knocking | milage per liter (km/l) | smoke observed in exhaust | Engine temp. as indicated by temp. gauge |
| 1 | gasoline, premium | normal about 2 sec. | fast and good | barely acceptable | rattling when accelerating | 9.2 | yes | L M H o o o / |
| 2 | pure methanol | difficult about 4 sec | unsatisfactory | bad | rattling | 4.1 | no | o o o \ |
| 3 | methanol 95% alcohol derivative 5% | difficult about 3 sec | slow but acceptable | acceptable | none | 5.5 | no | o o o \ |
| 4 | methanol 90% alcohol derivative 10% | 2 sec. | acceptable | improved | none | 7.3 | no | o o o \ |
| 5 | methanol 84.5% alcohol derivative 15% aldehyde under 0.5% | 0.5 sec | fast and good | good | none | 9.3 | no | o o o \ |

TABLE 3-continued

| test No. | fuel used | ignition time required | starting momentum | slope climbing | knocking | milage per liter (km/l) | smoke observed in exhaust | Engine temp. as indicated by temp. gauge |
|---|---|---|---|---|---|---|---|---|
| 6 | methanol 70%<br>alcohol derivative 30%<br>aldehyde under 0.5% | 0.5 sec | fast and good | power increased | none | 9.3 | no | o o o \ |
| 7 | methanol 70%<br>alcohol derivative 30%<br>aldehyde under 0.5% | 0.5 sec | excellent | power increased | none | 9.3 | no | o o o \ |
| 8 | methanol 60%<br>alcohol derivative 40%<br>aldehyde under 0.5% | 0.5 sec | excellent | better power | none | 9.4 | no | o o o \ |
| 9 | methanol 50%<br>alcohol derivative 50%<br>aldehyde under 0.5% | 0.5 sec | excellent | increased with easiness | none | 9.4 | no | o o o \ |
| 10 | methanol 40%<br>alcohol derivative 60%<br>aldehyde under 0.5% | 0.5 sec | excellent | with easiness | none | 9.4 | no | o o o | |

From Table 3, it is apparent that the liquid fuel of the present invention is actually as practical as conventional premium gasoline, and the fuel having a composition of 84.5% methanol, 15% alcohol derivative, 0.5% aldehyde gives the most economic performance. Fuels of other composition ratio, i.e. by increasing alcohol and decreasing alcohol derivative content seem to give significant improvement. Pure methanol is not suitable for use in the car having the existing engine design since the milage/1 is poor (only 4.1 km/l or one half of that of other fuels).

EXAMPLE 11

Examples 8-10 are repeated except that ethanol is used in place of methanol in the composition. The results show some improvement in ignition, starting, climbing, knocking, milage and exhaust properties over those using methanol. Therefore, a conclusion can be drawn that the fuel composition of the present invention is featured by its content of the alcohol derivative of $C_3H_8O_2$.

What is claimed is:

1. A fuel composition comprising:
   (a) from about 40 to 95% by volume of a primary alcohol having 1 to 4 carbon atoms;
   (b) from about 5 to 60% by volume of a compound having the general formula

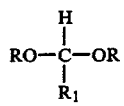

wherein R is —$CH_3$, —$C_2H_5$, —$C_3H_7$ or —$C_4H_9$, and $R_1$ is hydrogen or —$CH_3$; and
   (c) from about 0.001 to 1% by volume of an aldehyde having the general formula

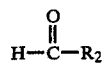

wherein $R_2$ is hydrogen, —$CH_3$, or —$C_2H_5$.

2. The fuel composition of claim 1 wherein the primary alcohol of (a) is present in an amount of from about 40 to 85% by volume, the compound of (b) is present in an amount of from about 15 to 60% by volume, and the aldehyde compound of (c) is present in an amount of from about 0.001 to 1% by volume.

3. The fuel composition of claim 2 wherein (a) is selected from the group consisting of methanol and ethanol; (b) is selected from the group consisting of

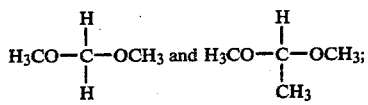

and (c) is selected from the group consisting of formaldehyde and acetaldehyde.

4. A process for preparing a synthetic fuel composition comprising:
   (1) reacting a first portion of a primary alcohol having 1 to 4 carbon atoms with one member of the group consisting of oxygen and air in the presence of Cu-Ag catalyst at a temperature of from about 300° to 450° C. and a pressure of from about 2 to 10 atm to form an aldehyde which is in liquid or vapor form; and
   (2) adding a second portion of the primary alcohol, which is in liquid or vapor form, to the products obtained in step (1) and reacting the so-obtained mixture in the presence of a halide catalyst at a temperature of from about 70° to 300° C., a pressure of from about 2 to 10 atm. and an alcohol: aldehyde molar ratio of about 2 to to 4:1 to form a fuel composition comprising:
   (a) from about 40 to 95% by volume of the primary alcohol;
   (b) from about 5 to about 60% by volume of a compound having the general formula

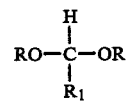

wherein R is —$CH_3$, —$C_2H_5$, —$C_3H_7$ or —$C_4H_9$; and $R_1$ is hydrogen or —$CH_3$; and
   (c) from about 0.001 to 1% by volume of an aldehyde having the general formula

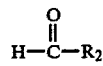

wherein $R_2$ is hydrogen, —$CH_3$ or —$C_2H_5$.

5. The process of claim 4 wherein the primary alcohol is methanol and the aldehyde is formaldehyde.

6. The process of claim 4 wherein the primary alcohol is methanol and the aldehyde is acetaldehyde.

7. The process of claim 4 wherein the primary alcohol is ethanol and the aldehyde is formaldehyde.

8. The process of claim 4 wherein the primary alcohol is ethanol and the aldehyde is acetaldehyde.

9. The process of claim 5, 6, 7, or 8 wherein the alcohol and the aldehyde are both in vapor form.

10. The process of claim 5, 6, 7, or 8 wherein the alcohol and the aldehyde are both in liquid form.

11. The process of claim 5, 6, 7, or 8 wherein the alcohol is in liquid form and the aldehyde is in vapor form.

12. The process of claim 5, 6, 7, or 8 wherein the alcohol is in vapor form and the aldehyde is in liquid form.

13. A process for preparing the fuel composition of claim 1, wherein the alcohol is methanol, comprising:
(1) reacting carbon dioxide with hydrogen to form methanol;
(2) reacting a portion of the methanol formed in (1) with oxygen or air in the presence of a Cu-Ag catalyst to form an aldehyde; and
(3) reacting the aldehyde formed in (2) with the remaining methanol formed in (1) in the presence of a gaseous halide catalyst to form the fuel composition.

14. A method of operating on internal combustion engine comprising feeding as fuel to the engine the composition of any one of claims 1, 2, 3, 15 and 16.

15. The fuel composition of claim 3 wherein component (a) is methanol and is present in an amount of about 84.5% by volume; component (b) is formal and is present in an amount of about 15% by volume; and component (c) is formaldehyde and is present in amount of about 0.5% by volume.

16. The fuel composition of claim 3 wherein component (a) is methanol and is present in an amount of about 68% by volume; component (b) is formal and is present in an amount of about 31.4% by volume; and component (c) is formaldehyde and is present in amount of about 0.6% by volume.

* * * * *